United States Patent [19]

Lien et al.

[11] Patent Number: 4,665,147

[45] Date of Patent: May 12, 1987

[54] NOVEL METHACRYLATED SILOXANES

[75] Inventors: Qcheng S. Lien, So. Windsor; Steven T. Nakos, East Hartford, both of Conn.

[73] Assignee: Loctite Corporation, Newington, Conn.

[21] Appl. No.: 654,058

[22] Filed: Sep. 24, 1984

Related U.S. Application Data

[63] Continuation-in-part of Ser. No. 509,568, Jun. 30, 1983, abandoned.

[51] Int. Cl.$^4$ ............................................. C08G 77/06
[52] U.S. Cl. ...................................... 528/15; 528/26; 528/31; 528/32; 556/437; 556/440
[58] Field of Search ................... 528/26, 31, 32, 15; 556/437, 440

[56] References Cited

U.S. PATENT DOCUMENTS

| | | | |
|---|---|---|---|
| 2,793,223 | 5/1957 | Merker | 526/279 |
| 2,898,361 | 8/1959 | Barnes | 528/26 |
| 2,922,806 | 1/1960 | Merker | 528/26 |
| 2,922,807 | 1/1960 | Merker | 528/26 |
| 2,956,044 | 10/1960 | Merker | 526/279 |
| 3,577,264 | 5/1971 | Nordstrom | 428/334 |
| 3,767,690 | 10/1973 | Speier | 528/30 |
| 3,878,263 | 4/1975 | Martin | 528/32 |
| 4,035,355 | 7/1977 | Baney | 528/24 |
| 4,139,548 | 2/1979 | Tanaka et al. | 556/437 |
| 4,348,454 | 9/1982 | Eckberg | 428/334 |
| 4,504,629 | 3/1985 | Lien et al. | 525/193 |
| 4,575,545 | 3/1986 | Nakos et al. | 528/15 |
| 4,575,546 | 3/1986 | Klemarczyk et al. | 528/15 |

FOREIGN PATENT DOCUMENTS

| | | |
|---|---|---|
| 949126 | 2/1964 | United Kingdom . |
| 1323869 | 7/1973 | United Kingdom . |
| 1384898 | 2/1975 | United Kingdom . |

OTHER PUBLICATIONS

Speier et al, J. Am. Chem. Soc., 79 974 (1957).
Ryan et al, J. Am. Chem. Soc., 82 3601 (1960).

*Primary Examiner*—Melvyn I. Marquis
*Attorney, Agent, or Firm*—Vidas & Arrett

[57] ABSTRACT

Methacrylated siloxanes are prepared by hydrosilation of beta(allyloxy)ethyl methacrylate using a silicon hydride functional siloxane. Propene elimination is not a significant side reaction of the method. Methacrylated silicones prepared in accordance with the invention are capable of anaerobic cure.

8 Claims, 2 Drawing Figures

NOVEL METHACRYLATED SILOXANES

This application is a continuation-in-part of copending application Ser. No. 509,568, filed June 30, 1983, now abandoned.

BACKGROUND OF THE INVENTION

The method of the present invention comprises reacting a siloxane having silicon hydride functionality and at least two repeat units, at least one of which has the formula

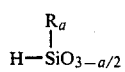

where R is an organo group and a is 1 or 2, with beta(allyloxy)ethyl methacrylate in the presence of an amount of hydrosilation catalyst effective for catalyzing a hydrosilation reaction between the allyl group on said methacrylate and said silicon hydride functional siloxane. Preferably the siloxane compound with silicon hydride functionality is a polyorganosiloxane with a molecular weight of 2500 or more, suitably 20,000 or more. Preferred organo groups are hydrocarbon groups such as methyl and phenyl groups. Other typical organo substituents for siloxane polymers, such as trifluoropropyl, methoxy or acetoxy groups may also be included.

This invention relates to polyorganosiloxane polymers (silicones) which have methacrylate functionality thereon.

Methacrylate functional organosiloxane compounds and polymers are desirable because they have faster and more versatile free radical cure characteristics than do the commercially available vinyl silicones. As described in U.S. Pat. Nos. 2,956,044 and 4,035,355, methacrylate functional silicones can be formulated with other unsaturated monomers to give monomer compositions or cured polymers with unique and desirable properties. U.S. Pat. No. 4,035,355 describes anaerobically curing compositions of methacrylate functional siloxane polymers. U.S. Pat. No. 3,577,264 describes radiation curable film-forming paint binders utilizing acrylate or methacrylate functional siloxanes. Other patents describing methods of preparation or uses for methacrylate functional siloxanes include U.S. Pat. Nos. 2,793,223; 2,898,361; 2,922,806; and 2,922,807, and 4,348,454 and U.K. Pat. Nos. 1384898 and 1323869.

In U.K. Pat. No. 949,126 there are described hydrolyzable silane compounds used as adhesion promoters for glass fiber reinforcing materials, some of which are prepared by hydrosilation of allyl-functional methacrylates such as allyl-methacrylate and beta(allyloxy)ethyl methacrylate. However, hydrosilation of allyl-substituted compounds has elsewhere been observed can be complicated by competing side reactions such as propene elimination unless the reacting silicon hydride contains strong electron withdrawing groups such as chlorine or carboxyl. See Speier, J. L., et al., J. Am. Chem. Soc., 79 1974 (1957); and Ryan, J. W., et al., J. Am. Chem. Soc., 82, 3601 (1960).

In U.S. Pat. No. 3,878,263 there are described acrylate and methacrylate functional siloxanes prepared from hydrolyzable acrylic functional silanes. The silanes may be prepared by hydrosilation of acrylic esters of unsaturated alcohols. Alternatively, the silanes may be prepared by reacting an alkoxy or hydroxy chloroalkyl silane with a tertiary amine salt of acrylic or methacrylic acid.

It is possible to prepare methacrylate functional silicones by hydrosilation of allyl methacrylate with silicon hydride functional polyorganosiloxane polymers, but, consistent with published reports on allyl hydrosilations, it has been observed that the process consistently yields a product in which about 30% of the methacrylate groups grafted onto the polymer are hydrolyzable. These groups are believed to have the following structure (where the hydrosilating groups were methylhydrosiloxane groups).

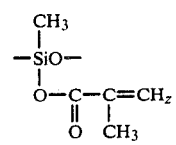

The presence of these hydrolyzable methacrylate groups produces a number of problems when the polymer is exposed to moisture, including loss of methacrylate functionality and increase in viscosity of the uncured polymer due to siloxy crosslinking.

The problem of propene elimination when allyl esters are hydrosilated is also recognized in U.S. Pat. No. 3,767,690 to Speier where organosilicon cinnamates were prepared from allyl cinnamates and organosilicon compounds which have mercapto functionality instead of SiH functionality.

When methallyl methacrylate is substituted for allyl methacrylate the propene elimination problem is eliminated but hydrosilation occurs at both ends of the molecule.

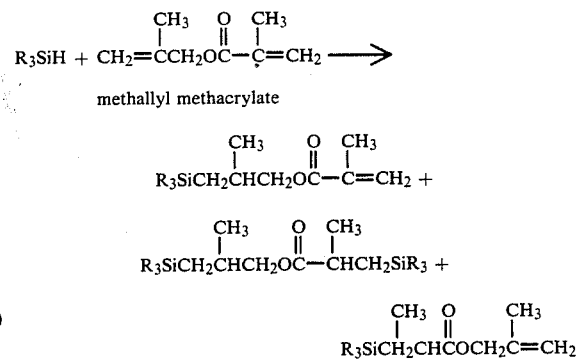

SUMMARY OF THE INVENTION

The present invention encompasses a method of preparing methacrylate functional organosiloxanes by hydrosilation of an allyl functional methacrylate compound with a silicon hydride functional siloxane. The allyl functional methacrylate which is used in the invention is beta(allyloxy)ethyl methacrylate which has unexpectedly been found to be successfully hydrosilated across the allyl double bond in substantially quantitative yield with no observable production of hydrolyzable methacrylate groups.

The invention further encompasses the novel methacryloxyethyleneoxypropyleneyl silicones produced by the inventive method and the cured products thereof.

DETAILED DESCRIPTION OF THE INVENTION

Figure 1:
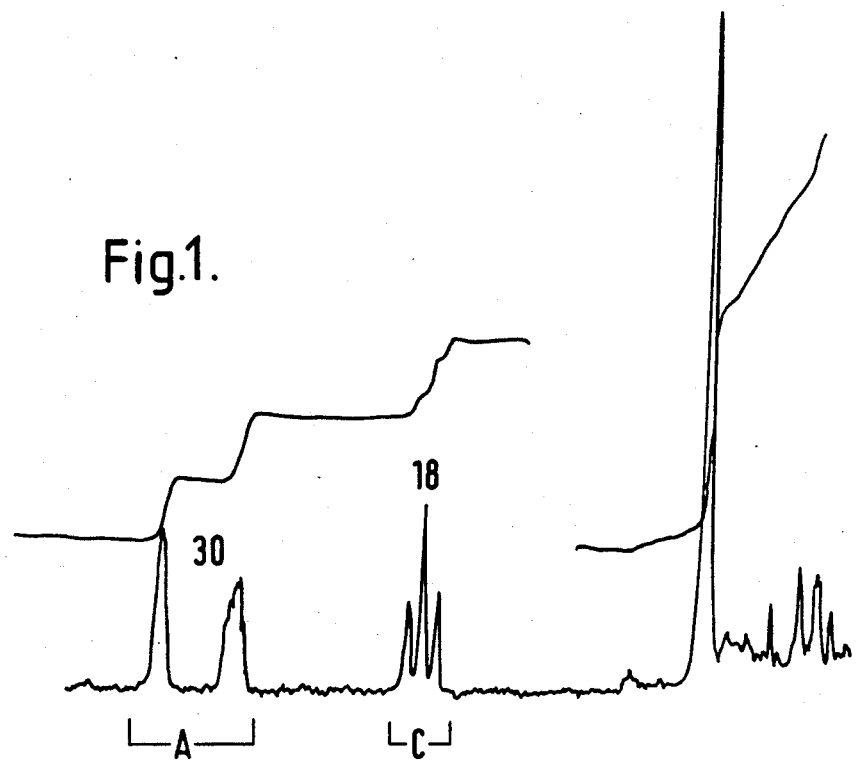
FIG. 1 is a 60 MHz NMR scan of a methacrylated polydimethylsiloxane prepared from allylmethacrylate.

The method of the present invention comprises reacting a siloxane having silicon hydride functionality and at least two repeat units, at least one of which has the formula

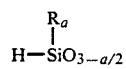

where R is an organo group and a is 1 or 2, with beta(allyloxy)ethyl methacrylate in the presence of an amount of hydrosilation catalyst effective for catalyzing a hydrosilation reaction between the allyl group on said methacrylate and said silicon hydride functional siloxane. Preferably the siloxane compound with silicon hydride functionality is a polyorganosiloxane with a molecular weight of 2500 or more, suitably 20,000 or more. Preferred organo groups are hydrocarbon groups such as methyl and phenyl groups. Other typical organo substituents for siloxane polymers, such as trifluoropropyl methoxy or acetoxy groups may also be included.

The hydrosilation of beta(allyloxy)ethyl methacrylate may be accomplished with silicon hydride functional siloxane polymers or low molecular weight analogs such as 1,3,5,7-tetramethylcyclotetrasiloxane and tetramethyldisiloxane. A noble metal hydrosilation catalyst is used, preferably a platinum catalyst. Reaction temperatures should be kept below about 100° C. in order to prevent thermal polymerization of the methacrylate groups.

Examples 1, 2 and 3 describe synthesis with tetramethyldisiloxane, a commercially available silicone hydride functional siloxane polymer and a specially synthesized SiH functional polyorganosiloxane, respectively.

EXAMPLE 1

4.0 grams tetramethyldisiloxane (0.03 moles) in 10 ml toluene was added gradually to a moisture protected flask containing 20.0 grams beta(allyloxy)ethyl methacrylate (0.12 moles), 0.50 grams 2% $H_2PtCl_6.6H_2O$ in butyl acetate and 0.05 grams phenothiaziane in 50 ml toluene.

The reaction was heated to 80° C., producing an exotherm between 85° C. and 89° C. for one hour. After the exotherm subsided, temperature was maintained at 80° C. for three additional hours when an IR scan showed no SiH stretch at 2200 cm$^{-1}$. The mixture was cooled, stripped with a rotary evaporator to remove toluene and deep-stripped at 80° C. and 0.35 mm.

This product had a tendency to polymerize during the deep-strip operation indicating that additional polymerization inhibitor should be added prior to the deep-stripping step.

EXAMPLE 2

5.0 grams of a commercially available 2500MW polydimethylsiloxane having 7 methyl hydrosiloxane units per molecule randomly distributed, (0.128 moles SiH), 2.18 grams beta-(allyloxy)ethyl methacrylate (0.128 moles) and 0.5 grams of a 2% solution of chloroplatinic acid in butyl acetate were mixed with 25 mls toluene and 0.3 grams hydroquinone and heated to 70° C. under dry hydrogen for three hours. At the end of this time, IR showed no SiH stretch at 2200 cm$^{-1}$. The mixture was cooled, stirred overnight with 2 grams activated basic alumina and then filtered through Celite, stripped to remove solvent, and deep-stripped to give 6.50 grams product.

The ability of this product to cure with an anaerobic acrylic cure system was demonstrated as follows. 5 grams of product was mixed with 2 drops (about 0.2 g) of cumene hydroperoxide, 1 drop of a 50% solution of saccharin in dimethylsulfoxide and 1 drop of dimethyl-p-toluidine. The mixture was applied to 6 strips of one inch wide sandblasted steel which were overlapped at a 90° angle by six additional one inch wide steel strips, three of which had been primed with a commercial primer based on mercaptobenzothiazole and dimethyl-p-toluidine. After 24 hours at room temperature, all had fixtured. There were no gross differences between the primed and unprimed sets, demonstrating that the methacrylated silicone products of the invention are capable of anaerobic cure on steel.

EXAMPLE 3

A polydimethylsiloxane polymer having a theoretical molecular weight of 20,000 and 6.8 methylhydrosiloxane units per molecule was prepared by stirring at room temperature for 2 days a mixture of 50.00 grams octamethylcyclotetrasiloxane, 1.06 grams tetramethylcyclotetrasiloxane, 0.42 grams hexamethyldisiloxane and 0.13 grams trifluoromethane sulfonic acid. After 2 days the mixture was diluted with 150 ml ether and washed with 3 grams $NaHCO_3$ in 50 ml water. The organic layer was washed twice with 50 ml water portions, dried over sodium sulfate, filtered and stripped to give 47.1 grams of product.

A methacrylated silicone in accordance with the invention was prepared from the polymer of the previous paragraph by mixing 10.00 grams of polymer, 0.51 grams beta-(allyloxy)ethyl methacrylate, 0.5 grams of a 2% chloroplatinic acid solution in butyl acetate and 0.03 grams hydroquinone with 25 ml toluene and heating the mixture to 70° C. under $N_2$ with stirring for 3 hours. The reaction mixture was then stirred overnight at room temperature with activated basic alumina. The alumina was filtered off through Celite, stripped to remove solvent and then deep-stripped as in Examples 1 and 2 to give 8.9 grams of a light brown product.

EXAMPLE 4

Figure 2:
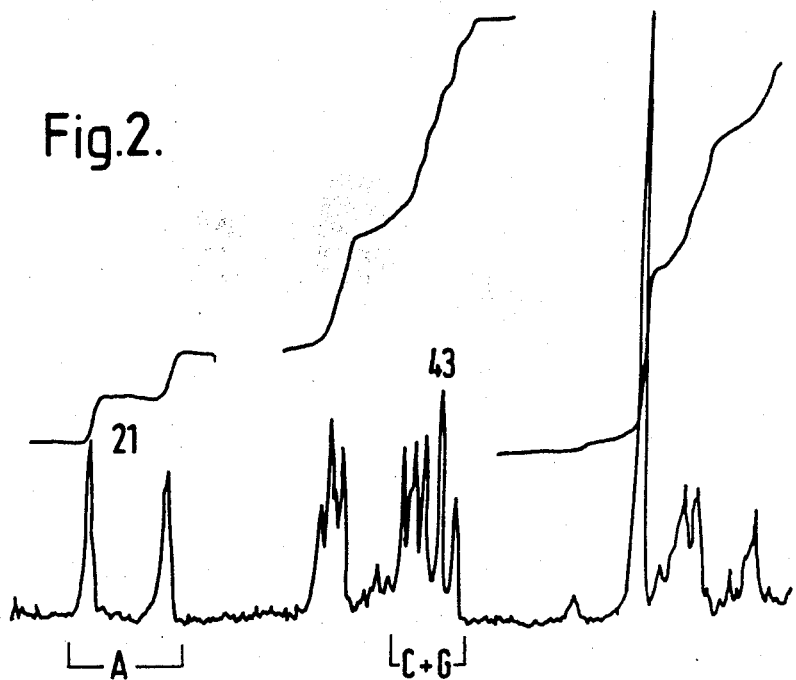
FIG. 2 is a 60 MHz NMR scan of a methacrylated polydimethylsiloxane prepared from beta(allyloxy)ethyl methacrylate.

Allyl methacrylate and beta(allyloxy)ethyl methacrylate were compared for propene elimination during hydrosilation as follows. Both esters were hydrosilated with a silicon hydride functional polydimethylsiloxane as in Example 2 except that mole ratios of esters to SiH were 1.05/1 and activated alumina was not used in the workup. NMR scans of the products were obtained using a 60 mhz NMR. The portions of those scans between about 1 and 7δ are shown in FIGS. 1 and 2 for the allyl methacrylate and beta(allyloxy)ethyl methacrylate products, respectively. The hydrogen atoms were labeled as follows for the two products:

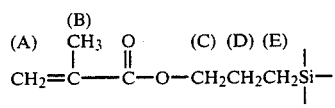

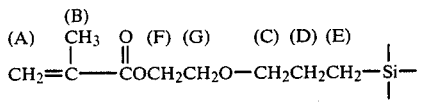

The NMR scan of the allyl methacrylate product, FIG. 1, gave a clean separation between methacrylate methylene group A and propyl methylene group C as shown in FIG. 1. Integration of these peaks gave a ratio of C/A=18/30. The theoretical ratio is 1/1, indicating substantial propene elimination. The methacryloxy siloxane product resulting from the propene elimination was further evidenced by the strong methacrylic acid odor which the product developed when exposed to atmospheric moisture overnight.

The NMR scan of the beta(allyloxy)ethyl methacrylate product, FIG. 2, showed clean separation for the methacrylate methylene hydrogens (A) and a complex combined peak for propyl and ethyl methylene hydrogens (C) and (G). The theoretical ratio of C and G to A was 2/1. The ratio found was 43/21, demonstrating that propene elimination did not occur.

In addition to the chloroplatinic acid used in the examples above, other hydrosilation catalysts may be used in the preparation of the inventive siloxanes. Examples are platinum, hydrocarbon platinum complexes and rhodium complexes. Platinum based catalysts are preferred at levels between 10 ppm and 500 ppm platinum, preferably between 50 ppm and 300 ppm.

We claim:

1. A method of preparing a methacrylated organosiloxane compound comprising reacting an organosiloxane compound having silicon hydride functionality comprising a plurality of repeat units of the formula:

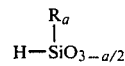

where R is an organo group and a is 1 or 2, with beta(allyloxy)ethyl methacrylate in the presence of an amount of hydrosilation catalyst effective for catalyzing a hydrosilation reaction between the allyl group on said methacrylate and said silicon hydride functional organosiloxane.

2. A method as in claim 1 wherein a hydrosilation catalyst is selected from platinum-based and rhodium-based catalysts.

3. A method as in claim 2 wherein said catalyst is chloroplatinic acid.

4. A method as in claim 1 wherein the silicon hydride functional siloxane compound is a polyorganosiloxane having a molecular weight of 2500 or more.

5. A method as in claim 2 wherein the hydrosilation catalyst is selected from platinum and hydrocarbon platinum complexes.

6. A method as in claim 1 wherein R is a hydrocarbon group.

7. A method as in claim 6 wherein R is methyl.

8. A method as in claim 1 wherein said silicon hydride functional siloxane is selected from tetramethyldisiloxane, 1,3,5,7-tetramethylcyclotetrasiloxane and polydimethyl silicones containing a plurality of methylhydrosiloxane repeat units.

* * * * *